United States Patent [19]
Smith et al.

[11] Patent Number: 5,831,109
[45] Date of Patent: Nov. 3, 1998

[54] POLYALKYLALUMINOXANE COMPOSITIONS FORMED BY NON-HYDROLYTIC MEANS

[75] Inventors: Gregory M. Smith, Danbury, Conn.; Stanley W. Palmaka, Yonkers, N.Y.; Jonathan S. Rogers, Belvidere, N.J.; Dennis B. Malpass, La Porte, Tex.

[73] Assignee: Akzo Nobel nv, Arhnem, Netherlands

[21] Appl. No.: 576,892

[22] Filed: Dec. 22, 1995

[51] Int. Cl.$^6$ .............................. C07F 5/06; B01J 31/00
[52] U.S. Cl. ................... 556/179; 556/182; 556/190; 502/117; 502/152
[58] Field of Search .................. 556/179, 182, 556/190; 502/117, 152

[56] References Cited

U.S. PATENT DOCUMENTS 5,235,081  8/1993  Sangokoya ............... 556/179

OTHER PUBLICATIONS

S. Pasynkiewicz, "Alumoxanes: Synthesis, Structures, Complexes and Reactions", Polyhedron, 1990, pp. 429–453.

Comprehensive Organometallic Chemistry II: A Review of the Literature 1982–1994, E.W. Abel et al., eds., Pergamon, 1995, pp. 450, 452–453, and 498–499.

E.A. Jeffery et al., "Hemi–Alkoxides from Reactions of Trimethylaluminum with Aldehydes or Ketones", Aust. J. Chem., 1970, 23, 715–724.

A. Meisters et al., "Exhaustive C–Methylation of Ketones by Trimethylaluminum", Aust. J. Chem., 1974, 27, 1655–1663.

A. Meisters et al., "Exhuastive C–Methylation of Carboxylic Acids by Trimethylaluminum: A New Route to t–Butyl Compounds", Aust. J. Chem., 1974, 27, 1665–1672.

D.W. Harney et al., "C–Methylation of Alcohols by Trimethylaluminum", Aust. J. Chem., 1974, 27, 1639–1653.

A. Meisters et al., "Exhaustive Methylation by Trimethylaluminum", J.C.S. Chem. Comm., 1972, 595–596.

*Primary Examiner*—Porfirio Nazario-Gonzalez
*Attorney, Agent, or Firm*—Richard P. Fennelly; Louis A. Morris

[57] ABSTRACT

The present invention relates to a process which comprises the non-hydrolytic transformation of an aluminoxane precursor composition, comprising carbon-to-oxygen bonds which can be alkylated by an alkylaluminum moiety, into a catalytically useful aluminoxane composition. In one embodiment of this invention, the catalytically useful aluminoxane composition is a polymethylaluminoxane composition substantially free of trimethylaluminum. The intermediate precursor is formed by the reaction of a trialkylaluminum compound, or a mixture of trialkylaluminum compounds, and a compound containing a carbon-to-oxygen bond, such as an alcohol, ketone, carboxylic acid, or carbon dioxide. Either unsupported or supported polymethyl-aluminoxane compositions can be formed.

13 Claims, No Drawings

POLYALKYLALUMINOXANE COMPOSITIONS FORMED BY NON-HYDROLYTIC MEANS

BACKGROUND OF THE INVENTION

The present invention relates to a novel synthesis of aluminoxanes by non-hydrolytic means and to novel aluminoxane compositions. Aluminoxanes are well known as components for olefin polymerization catalysts.

Aluminoxane compounds are chemical species that incorporate Al—O—Al moieties. While a wide range of aluminoxane species are known, their exact structures are not precisely known. The following structures (where R is alkyl and X is an integer of from about 1 to about 40) have been depicted:

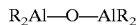

$R_2Al-O-AlR_2$

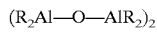

$(R_2Al-O-AlR_2)_2$

$R-(RAlO)_x-AlR_2$

$(RAlO)_x$

Cyclic and cage cluster structures have also been proposed. Such materials, as would be recognized by the person of ordinary skill in the art are complex mixtures of various species which can easily undergo dynamic exchange reactions and structural rearrangements. A recent review of these materials was authored by S. Pasynkiewicz and appears in Polyhedron, Vol. 9, pp. 429–453 (1990).

Methylaluminoxanes, sometimes termed "polymethylaluminoxanes" (PMAOs) are well known materials with wide utility in olefin polymerization using single-site, or metallocene-based, polymerization catalyst systems (See, for example, Col. 1, lines 14–29 of U.S. Pat. No. 4,960,878 to C. C. Crapo et al.). PMAOs are conventionally prepared by controlled hydrolysis of trimethylaluminum (TMAL). Generally, hydrolysis occurs with some loss of aluminum to insoluble species. Generally, PMAOs also have very low solubility in aliphatic solvents, which limits their utility, as well as poor storage stability for solutions containing them. (See, for example, Col. 1, lines 30–46 of U.S. Pat. No. 4,960,878). Finally, it is generally polymethylaluminoxanes that have been the most useful products of this general class of material: other alkylaluminoxanes do not work as well. Since TMAL is an expensive starting material, the resulting PMAO is expensive.

The problems of low yield, poor solubility, poor storage stability, and expensive reagents in preparation of PMAO have previously been attacked, with only limited success, in several ways. One method was to make predominantly PMAO, but include some components from hydrolysis of other aluminum alkyls, to form the so-called "modified methylaluminoxane" (MMAO). This yields predominantly methyl-containing aluminoxanes in improved yields, with improved solution storage stability as well as improved solubility in aliphatic solvents, at lower cost. However, since alkyl groups other than methyl are present, these materials are not always as effective as conventional PMAO.

The prior art contains certain disclosures which are deemed to be particularly germane to the present invention, including a series of related publications by T. Mole and coworkers (E. A. Jeffrey et al., Aust. J. Chem. 1970, 23, 715–724; A. Meisters et al., Journal of the Chemical Society, Chem. Comm. 1972, 595–596; D. W. Harney et al., Aust. J. Chem. 1974, 27, 1639–1653; A. Meisters et al., Aust. J. Chem. 1974, 27, 1655–1663; and A. Meisters et al., Aust. J. Chem. 1974, 27, 1665–1672) which describe the exhaustive methylation of oxygen-containing organic substrates by trimethylaluminum (hereinafter abbreviated as "TMAL" for simplicity). Some of the reactions that these publications report are listed hereinbelow:

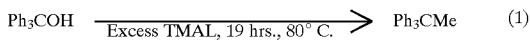

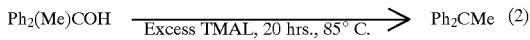

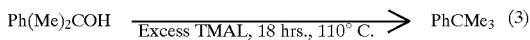

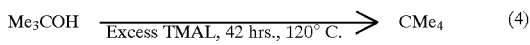

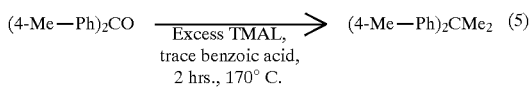

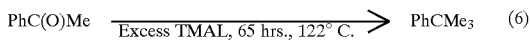

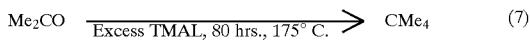

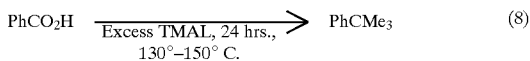

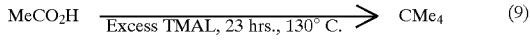

This work focused on conversion of the organic substrates, and only speculates occasionally on the aluminum containing products formed. Some of the comments they do make include, e.g., Equation (6) of Meisters et al.(Aust. J. Chem. 1974, 27, 1655–1663) which shows [$Me_2AlOAlMe_2$] as a speculative product; as well as Equation (6) of Meisters et al. (Aust. J. Chem. 1974, 27, 1665–1672) which also shows [$Me_2AlOAlMe_2$] as a speculative product. Another relevant comment made in these disclosures is that these reactions do not remain homogeneous (see the footnote on page 1643 of Harney et. al, Aust. J. Chem. 1974, 27, 1639–1653).

Another relevant comment appears in Comprehensive Organometallic Chemistry II, E. W. Abel et al., eds., New York N.Y., Pergamon, 1995, Vol. 1, p. 452 where several preparations of aluminoxanes are given, including those set forth in Equations (54)–(57) and Scheme 8. Aluminoxanes of these preparative methods, however, are said to be unsuitable as cocatalysts for single-site catalysts.

Another problem well known in the art is the inevitable presence of trimethylaluminum (TMAL) in the polymethylaluminoxane (PMAO) product. In particular, L. Resconi et al, Macromol. 1990, 23, 4489–4491 and the references cited therein show that PMAO prepared in the normal manner contains both methylaluminoxane species as well TMAL species. These researchers based their conclusion on, among other things, the presence of two signals in the $^1H$ NMR of PMAO. FIG. 1, which forms a part of the present specification, illustrates the $^1H$ NMR of commercially available PMAO with the spectrum being composed of both a broad peak, attributed to methylaluminoxane species, and a distinct second peak, attributed to trimethylaluminum species. M. S. Howie, "Methylaluminoxane and Other Aluminoxanes-Synthesis, Characterization and Production", Proceedings, MetCon '93, pp. 245–266, Catalyst Consultants Inc., Houston, Tex. 1993, has also noted that PMAO invariably contains TMAL. For instance, on page 247 it is stated that "MAO always contains some amount of TMA". Further, Howie notes that "total removal of TMA from MAO has not been demonstrated, and reduction to low levels creates other problems".

SUMMARY OF THE INVENTION

The present invention, in one embodiment, relates to a novel composition which is a catalytically useful composition comprising alkylaluminoxane which is substantially free of trialkylaluminum content. The $^1$H NMR of the product of this invention, for example, does not separately distinguish TMAL as a species which is present therein.

This invention also relates to a process for forming aluminoxanes from a particular type of aluminoxane precursor composition, which will be described in greater detail below, using non-hydrolytic means (e.g., by thermal and/or catalytic means). The intermediate aluminoxane precursor composition, which is ultimately capable of being transformed by the aforementioned non-hydrolytic means to the desired aluminoxane product, is formed by treating a trialkylaluminum compound, or mixtures thereof, with a reagent that contains a carbon-oxygen bond. This treatment to form the intermediate aluminoxane precursor composition is followed by the aforementioned non-hydrolytic transformation of the intermediate aluminoxane precursor composition to give a catalytically useful aluminoxane composition. It should be clearly understood that the process described herein can be used to form the novel type of alkylaluminoxane referred to in the first paragraph of this section of the specification as well as conventional polymethylaluminoxane compositions that are not substantially free of TMAL as a species which is present therein as measured by the $^1$H NMR spectrum of the product. It should also be recognized that the process described herein is useful for the formation of alkylaluminoxanes, in general, as well as the formation of polymethylaluminoxane. In most cases it may be desirable to obtain a polymethylaluminoxane product with a low free TMAL content. However, the amount of free TMAL remaining in the aluminoxane composition may be adjusted from very low levels to over 50% by controlling the stoichiometry and reaction conditions in the process.

The present invention, in a preferred embodiment, enables one to produce polymethylaluminoxane compositions of improved solution stability which also have the desirable feature of compatibility with aliphatic hydrocarbon solvents, such as hexane, heptane, octane or decane. The process allows for high recoveries (yields) of aluminum values in making the desired product. Also, the process produces an methylaluminoxane product giving high activities in polymerization of olefin monomer(s).

DESCRIPTION OF THE DRAWINGS

The Drawings which form a portion of this Specification are provided herewith to further illustrate certain attributes of the present invention. FIG. 1 illustrates the $^1$H NMR of commercially available PMAO with the spectrum being composed of both a broad peak, attributed to methylaluminoxane species, and a distinct second peak, attributed to trimethylaluminum species. FIG. 2 shows a novel PMAO product that can be made, in accordance with one particular embodiment of the process of the present invention, which is easily handled and which performs well, but which is substantially free of TMAL as a species that can be separately distinguished by $^1$H NMR.

DESCRIPTION OF PREFERRED EMBODIMENTS

As just mentioned, preferred embodiments of the present invention relate to (1) a process for forming, by the non-hydrolytic conversion of suitably constituted alkylaluminoxane precursor compositions, catalytically useful methylaluminoxane compositions, and (2) polymethylaluminoxane compositions which are substantially free of trimethylaluminum content and which are catalytically useful methylaluminoxane compositions.

The intermediate precursor composition is an organoaluminum composition which is constituted such that it contains alkyl groups, initially bound to aluminum which are capable of alkylation of groups, also contained in the precursor, which contain a carbon-to-oxygen bond. When the alkylation of such carbon-oxygen containing groups occurs, the oxygen atoms contained in such groups in the precursor are incorporated into alkylaluminum moieties during that part of the present process in which the intermediate precursor is transformed to the desired aluminoxane product.

It will be appreciated by a person of ordinary skill in the art that there are many ways of forming the intermediate precursor composition which must contain some amount of alkylaluminum groups as well as some carbon which is chemically bound to oxygen and susceptible to alkylation by an alkylaluminum group. For the purposes of illustrating the nature of these precursor compositions, the following discussion will provide examples of methods for forming suitable compositions of that type. This discussion, however, should not be construed as limiting the present invention to the particular methods which may be exemplified herein, for example, for preparing the preferred aluminoxane precursor composition, which may incorporate a wide range of chemical species therein without precisely known chemical structure. For instance, as will become apparent from the following description, if a ketone, such as benzophenone, is reacted with a trialkylaluminum compound, such as trimethylaluminum, an addition reaction will occur. The result will be a composition containing alkylaluminum groups (in this case, methylaluminum) and functional groups where carbon is also bound to oxygen (in this case, a 1,1-diphenyl-ethoxy functional group):

Analogous precursor compositions can be formed in alternative ways, as will be described in more detail below. As another example, a salt metathesis reaction can be depicted as follows:

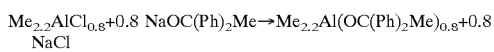

As earlier mentioned, the precursor intermediate composition can be formed by using a reagent, containing a carbon-to-oxygen chemical bond. Suitable reagents which can be used can be selected from the alcohols, the ketones, and the carboxylic acids as representative examples. A particularly suitable inorganic reagent which has been found to work is carbon dioxide.

In the preferred embodiment of the present invention, this precursor composition is formed by treating trimethylaluminum with an oxygenated organic compound such as an alcohol, ketone, carboxylic acid or carbon dioxide. In the case of carboxylic acids or carbon dioxide, some aluminoxane moieties will form (see, for example, copending application U.S. Ser. No. 08/545,078, filed on Oct. 19, 1995). In all these cases, as is well known in the art (see, for instance, the citations to exhaustive methylation given above, and references cited therein), alkoxyaluminum or arylalkoxyaluminum moieties will be formed. The following equations represent possible, non-limiting, examples of the reactions of trimethylaluminum and oxygenated organic molecules to form alkoxyaluminum or arylalkoxyaluminum-based aluminoxane precursor compositions (R and R' being the same or different and being selected from alkyl and/or aryl and TMAL indicating trimethylaluminum):

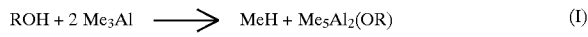

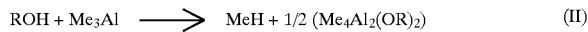

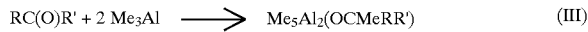

The most preferred embodiment of the present invention is to use a carboxylic acid or carbon dioxide as they form both a methylaluminoxane precursor containing the alkoxyaluminum or arylalkoxyaluminum moieties and the desired methylaluminoxane products.

Once this preferred methylaluminoxane precursor composition is formed, the key component of the present invention is the thermal and/or catalytic transformation of this precursor to form the desired catalytically useful methylaluminoxane composition. While the prior art teaches that these precursor compositions can be transformed to form exhaustively methylated organic derivatives, it does not disclose the formation of catalytically active aluminoxane compositions, nor does it teach the proper conditions to form such a catalytically useful composition comprising methylaluminoxane. A recent review in the prior art (Comprehensive Organometallic Chemistry II, Vol. 1, p. 452) suggests, in fact, that polymethylaluminoxane processes based on carboxylic acid reagents "do not produce aluminoxanes suitable for catalytic applications". The prior art additionally fails to recognize the aliphatic hydrocarbon solubility and improved storage stability characteristics of the preferred products of the process of the present invention as well as the possibility of manufacturing the novel low TMAL-containing product of certain embodiments of the instant invention. The prior art appears to be silent on exhaustive methylation of carbon dioxide. Furthermore, as the Examples provided hereinbelow illustrate, we have discovered conditions where this reaction remains homogeneous, in contrast to the heterogeneous examples of the prior art.

The present invention has also discovered that formation of PMAO, for example, by the present invention yields, in certain embodiments, a product substantially free of TMAL since separate signals for PMAO and TMAL are not observed in the $^1$H NMR spectrum of the product.

The process of the present invention produces high recoveries of aluminum as compared to hydrolytic processes for making aluminoxanes as conventionally known to the art. The process of the present invention also is capable of producing polymethylaluminoxane with improved storage stability as compared to hydrolytic processes for making aluminoxanes as conventionally known to the art. Finally, the process of this invention is capable of producing polymethylaluminoxane in high yield in the presence of aliphatic solvents, unlike hydrolytic processes for making aluminoxanes as conventionally known in the art.

The preferred method for transforming the methylaluminoxane precursor is to optionally add, or form in situ, a catalytically effective amount of methylaluminoxane with the precursor and heat the material at the lowest temperature sufficient to effect conversion to the desired methylaluminoxane composition in a reasonable amount of time. This reaction can also be facilitated by increasing the concentration of organometallic species by removing, or limiting in other ways, the amount of solvent, if solvent, which is an optional ingredient at this point in the process, is present.

The present invention, in its most preferred embodiment is a novel process, for forming catalytically useful polymethylaluminoxane with the resulting, polymethylaluminoxane composition, in certain embodiments being a novel polymethylaluminoxane composition which is substantially free of trimethylaluminum. This process comprises the thermal and/or catalytic transformation of an appropriately constituted precursor composition as earlier described. A preferred method for preparing the precursor composition is treatment of trimethylaluminum with a carboxylic acid or with carbon dioxide. However, as will be appreciated by a person of ordinary skill in the art, there are many other methods which can be used to prepare the precursor composition which is transformed into the desired final product.

If desired, supported polyalkylaluminoxane compositions can be prepared by conducting the aforementioned reaction in the presence of a suitable support material. Alternatively, supported alkylaluminoxanes may also be prepared by forming the alkylaluminoxanes of this invention in a discrete, separate step and subsequently allowing the alkylaluminoxane to react with the support material. Oxidic support materials, such as silica, are especially preferred.

As will be appreciated by the person of ordinary skill in the art, the aluminoxane products that can be made by the process of the present invention are useful as cocatalysts in those single-site (metallocene-based) catalyst systems which are useful in the polymerization of olefin monomers in a manner analogous to that in current use with the aluminoxane compositions that are currently known and used in that manner.

The present invention will be further illustrated by the Examples which follow.

EXAMPLES

Standard air-free glovebox and Schlenk line techniques were used. Polymerization tests were conducted in hexane at 85° C., under a total pressure of 150 psig (ethylene+hexane+hydrogen), using rac-ethylenebisindenylzirconium dichloride:trimethylaluminum 1:30 as the catalyst precursor component with the aluminoxane present at 1000:1 Al:Zr. Trimethylaluminum (37.2 wt % Al) and polymethylaluminoxane (PMAO) in toluene (9.0 wt % Al) were obtained from Akzo Nobel Chemicals Inc., Deer Park Tex., and used as received. Benzophenone and benzoic acid were obtained from Aldrich Chemical Co., placed under a nitrogen atmosphere, and otherwise used as received.

Example 1

A solution of trimethylaluminum (2.00 g trimethylaluminum, 15.6 g toluene) was treated with a solution of benzophenone (4.02 g benzophenone, 15.6 g toluene), and the resulting mixture heated at 60° C. for one and one half hours to give a solution of alkylaluminum arylalkoxides with the overall composition $((CH_6H_5)_2MeCO)_{0.8}AlMe_{2.2}$. Analysis of this product by $^1$H NMR showed it to be a mixture of the discrete compounds: $((C_6H_5)_2MeCO)_1AlMe_2$ and $((C_6H_5)_2MeCO)_1Al_2Me5$. This product could be heated, as is, for many hours at 60° C. and remain unchanged according to $^1$H NMR.

A catalytic amount of PMAO (0.35 g, 9.0 wt % Al) was added to the alkylaluminum arylalkoxide solution, and the mixture heated at 60° C. for 3.2 hours. At the end of this time, analysis by $^1$H NMR showed that alkoxy aluminum species were no longer present, and that aluminoxane moieties were present. An ethylene polymerization test, which normally yields about 700 kg PE/g Zr hr with conventional PMAO prepared by Akzo Nobel Chemicals Inc., gave 1380 kg PE/g Zr hr using this polymethylaluminoxane instead.

Example 2

A solution of trimethylaluminum (2.00 g trimethylaluminum, 3.10 g toluene) was treated with a solution of benzoic acid (1.35 g of benzoic acid in 18.4 g of toluene) at 0° C. Methane gas was evolved. Analysis by $^1$H NMR showed this mixture to contain PhMe$_2$COAl and Me-Al and Al—O—Al moieties. When this mixture was heated at 80° C. for twenty-four hours, no change occurred.

A catalytic amount of PMAO (0.83 g, 9.0 wt % Al) was added to the alkylaluminum alkoxide and aluminoxane solution, and solvent removed in vacuo, to give a clear, slightly viscous liquid. This liquid was heated at 80° C. for 1 hr and 55 minutes, to give a clear, amorphous, toluene soluble solid. Analysis by $^1$H NMR showed that alkoxy aluminum species were no longer present, and that aluminoxane moieties were present. As no insoluble aluminum-containing byproducts were formed, this preparation gave a quantitative yield of catalytically useful polymethylaluminoxane. In an accelerated aging test, conducted at 50° C., the polymethylaluminoxane prepared by this Example remained clear, homogeneous and free of gels for up to ten days, while a conventional, hydrolytically prepared, commercial PMAO showed gel formation within three to five days at the same temperature. An ethylene polymerization test gave 680 kg PE/g Zr hr using this polymethylaluminoxane.

Example 3

TMAL (15.00 g) was mixed with toluene (9.25 g) and was then reacted with carbon dioxide (3.74 g) at room temperature to form an alkoxyaluminum and alkylaluminoxane-containing PMAO precursor composition. This mixture was heated at 100° C. for twenty-four hours to give a clear, viscous liquid whose $^1$H NMR showed it to have been converted to PMAO. Alkoxyaluminum species were no longer detectable by NMR analysis. As no insoluble aluminum-containing byproducts were formed, this preparation gave a quantitative yield of catalytically useful polymethylaluminoxane. A polymerization test with this material yielded 2400 kg PE/g Zr hr in a thirty minute test.

Example 4

Using the same procedure that is described in Example 2, TMAL (8.00 g) in 9.51 g of toluene was treated with neat benzoic acid (5.40 g) to give an arylalkoxyaluminum-containing methylaluminoxane precursor. Heating of this mixture at 80° C. for five hours gave conversion to PMAO. As no insoluble aluminum-containing byproducts were formed, this preparation gave a quantitative yield of catalytically useful polymethylaluminoxane.

FIG. 1 shows the Me-Al region of a $^1$H NMR spectrum of conventional PMAO obtained from a commercial source. The spectrum clearly contains two signals, a broad signal due to methylaluminoxane species, and a sharper signal due to trimethylaluminum species. FIG. 2 shows the same region of the spectrum of PMAO prepared in this Example. Unlike the commercially available PMAO, the material of this invention shows only one broad signal in the depicted region. The product is substantially free of TMAL in that no distinct $^1$H NMR signal from TMAL is discernible.

Example 5

A solution of trimethylaluminum (8.0 g in 4.94 g of decane) was treated with carbon dioxide (1.9 g of carbon dioxide) over a period of eight hours. Analysis by $^1$H NMR showed this mixture to contain (CH$_3$)$_3$CO—Al, CH$_3$—Al, and Al—O—Al moieties. Heating this sample at 100° C. for twenty-four hours caused no change in the $^1$H NMR spectrum. However, when heated for five hours at 120° C., the reaction mixture became slightly hazy, forming a viscous liquid after cooling. Since it was not necessary to separate solid, aluminum-containing byproducts from this product, this preparation gave a quantitative yield of catalytically useful polymethylaluminoxane. Analysis by $^1$H NMR showed signals due to decane solvent, traces of residual t-butoxy signals, and a broad signal due to methylaluminoxane species.

An ethylene polymerization test gave 1100 kg PE/g Zr/hr using the polymethylaluminoxane prepared in this Example.

The foregoing Examples, since they merely illustrate certain embodiments of the present invention, should not be construed in a limiting sense. The scope of protection sought is set forth in the claims which follow.

We claim:

1. A process which comprises the non-hydrolytic transformation of an aluminoxane precursor composition, which comprises moieties containing carbon-to-oxygen bonds that can be alkylated by alkylaluminum moieties, to form a composition comprising catalytically useful alkylaluminoxane moieties.

2. The process of claim 1 where the aluminoxane precursor composition is formed by the reaction of a trialkylaluminum compound, or a mixture of trialkylaluminum compounds, and a compound containing carbon-to-oxygen bonds.

3. The process of claim 1 where the aluminoxane precursor composition is formed by the reaction of a trialkylaluminum compound, or a mixture of trialkylaluminum compounds, and carbon dioxide.

4. The process of claim 2 wherein the compound is selected from the group consisting of the alcohols, ketones, and the carboxylic acids.

5. The process of claim 1 wherein the precursor composition is thermally transformed and had been formed by the reaction of a trialkylaluminum compound, or a mixture of trialkylaluminum compounds, and carbon dioxide.

6. The process of claim 5 where the mixture of trialkylaluminum compounds comprises trimethylaluminum and one or more trialkylaluminum compounds comprising an alkyl group which comprises two or more carbon atoms.

7. The product formed by the process of any of claims 1 to 6.

8. A polymethylaluminoxane product formed by the process of any of claims 1 to 6.

9. The supported product formed by the process of any of claims 1 to 6.

10. The supported polymethylaluminoxane product formed by the process of any of claims 1 to 6.

11. The silica-supported polymethylaluminoxane product formed by the process of any of claims 1 to 6.

12. A catalyst composition for use in the polymerization of olefins which comprise the aluminoxane, optionally on a support, formed by the process of any of claims 1 to 6.

13. A catalyst composition for use in the polymerization of olefins which comprise a polymethylaluminoxane, optionally on a support, formed by the process of any of claims 1 to 6.

* * * * *